(12) United States Patent
Chin-Ly

(10) Patent No.: US 10,149,667 B2
(45) Date of Patent: Dec. 11, 2018

(54) EXOCERVICAL AND ENDOCERVICAL CELL SAMPLING DEVICE

(71) Applicant: DNA RESEARCH CENTRE (M) SDN BHD, Bangi, Selangor (MY)

(72) Inventor: Cindy Lim Chin-Ly, Selangor (MY)

(73) Assignee: DNA Research Centre (M) SDN BHD, Bangi, Selangor (MY)

( * ) Notice: Subject to any disclaimer, the term of this patent is extended or adjusted under 35 U.S.C. 154(b) by 278 days.

(21) Appl. No.: 15/029,460

(22) PCT Filed: Oct. 14, 2013

(86) PCT No.: PCT/MY2013/000181
§ 371 (c)(1),
(2) Date: Apr. 14, 2016

(87) PCT Pub. No.: WO2015/057049
PCT Pub. Date: Apr. 23, 2015

(65) Prior Publication Data
US 2016/0262734 A1    Sep. 15, 2016

(51) Int. Cl.
*A61B 5/00*         (2006.01)
*A61B 10/02*        (2006.01)
(Continued)

(52) U.S. Cl.
CPC .......... *A61B 10/0291* (2013.01); *A61B 10/04* (2013.01); *A61B 10/06* (2013.01);
(Continued)

(58) Field of Classification Search
CPC .. A61B 10/02; A61B 10/0291; A61B 10/0045
(Continued)

(56) References Cited

U.S. PATENT DOCUMENTS 3,776,219 A   12/1973  Brown
5,445,164 A   8/1995   Worthen et al.
(Continued)

FOREIGN PATENT DOCUMENTS

CN       201350076 Y    11/2009
EP         0995401 A1    4/2000
WO   WO 2011/152705 A1  12/2011

OTHER PUBLICATIONS

"Pap Test," Wikipedia, URL https://en.wikipedia.org/wiki/Pap_test (Published: Sep. 30, 2013).

*Primary Examiner* — Max Hindenburg
(74) *Attorney, Agent, or Firm* — Edwin D. Schindler

(57) ABSTRACT

A cervical cells sampling device includes a tubular sleeve with a first opening and an opposing second opening, an elongate rod having a retractable part with a mounting tip enclosed within the sleeve and a handle section extending out from the sleeve through the second opening. A cell collecting construct with a resilient sheath is stretched to cap onto the mounting tip of the rod and the stretched resilient sheath is in a constant contracting state that the cell collecting construct and portion of the retractable part are allowed to project out, or retract into sleeve, through the first opening by moving the handle section. A stripping member is fabricated within the sleeve to detach the resilient sheath from the mounting tip upon retracting the retractable part into the sleeve up to a predetermined level and the resilient sheath resumes original form once detached from the mounting tip, while prodding the rod back into the sleeve pushes the construct out of the sleeve.

4 Claims, 2 Drawing Sheets

(51) Int. Cl.
  *C12M 1/26*    (2006.01)
  *A61B 10/04*   (2006.01)
  *A61B 10/06*   (2006.01)
  *G01N 1/08*    (2006.01)
  *A61B 10/00*   (2006.01)

(52) U.S. Cl.
  CPC ..... *C12M 33/00* (2013.01); *A61B 2010/0074* (2013.01); *A61B 2010/0208* (2013.01); *G01N 2001/085* (2013.01)

(58) Field of Classification Search
  USPC .................................................. 600/569, 572
  See application file for complete search history.

(56) References Cited

U.S. PATENT DOCUMENTS

| | | | |
|---|---|---|---|
| 5,795,309 A * | 8/1998 | Leet ................... | A61B 10/0291 600/569 |
| 6,352,513 B1 * | 3/2002 | Anderson .......... | A61B 10/0045 600/569 |
| 6,387,058 B1 * | 5/2002 | Wallach ............. | A61B 10/0291 600/569 |

* cited by examiner

//EXOCERVICAL AND ENDOCERVICAL
CELL SAMPLING DEVICE

FIELD OF INVENTION

The present invention relates to a sampling device capable of collecting both exocervical and endocervical cells through a pliable cell collecting construct for further testing. Particularly, the disclosed sampling device is equipped with simple mechanism to release the cell collecting construct from the device for preparation of further testing without risking to contaminate the collected cell sample by unnecessary contact.

BACKGROUND OF THE INVENTION

Following effective and promotion on prognosis screening program for cervical cancers established in many countries, both incidence and death rate of cervical cancer have declined sharply worldwide in recent years. Conventionally, cervical exfolated cells was used to prepare cytological sample with a method known as Papanicolaou smear or Pap test. The Pap test has proven to be highly effective in the early detection of cervical pre-cancerous and cancerous growth. To accommodate huge market need, many sampling devices had been developed. These devices aim to provide better sampling of a full cell presentation with minimum discomfort or traumatic effect. For example; U.S. patent application Ser. No. 3776219 provides a cervical scrapper for self sampling that the collector portion of the scrapper is protected by flexible petal-like appendages from contamination during its withdrawal from the vagina. Similar device used for sampling cervical mucus is described in another U.S. patent application Ser. No. 4628941. Other types of sampling devices can be found in U.S. patent application Ser. No. 5253652 and Malaysian patent application no. 141032 which the devices have an embedded portion, to be pivoted through an actuator on the stem as, allocated for collecting exocervical cell samples.

Moreover, the collection techniques for Pap test have been modified lately for detection of human papilomavirus (HPV) in cervical specimen of the patients after having sufficient scientific findings shown statistically significant relation in between HPV infection and cervical cancer occurrence. HPV detection methods particularly discover copies of DNA fragment, in the collected specimen, belongs to the HPV to infer HPV infection. To proceed with HPV detection, the collected cervical specimen requires firstly to be stored in a preserving solution before subjecting to the HPV detection in the laboratory. While transferring the collected specimen to the preserving solution, it is important to ensure no cross-contamination occurred onto the specimen especially unnecessary contact made onto the specimen by other subject matter. Therefore, it is much preferred the sampling device is equipped with a mechanism facilitating specimen transfer with minimal contact with the external environment. Antonius et. al offers a sampling device for collecting cervical cell specimen in U.S. Pat. with publication No. 2006287610. The offered device carries a solution to flush the desired location followed by drawing back the flushed solution to acquire the targeted specimen.

SUMMARY OF THE INVENTION

The present invention aims to provide a sampling device for collecting cervical cell to be used for cervical cancer screening. Particularly, the disclosed invention has a cell collecting construct capable of extending into vagina of a user to conduct the cell collection and a protective sleeve is used in conjunction to shield the collected specimen in the withdrawal of the cell collecting construct.

Another object of the disclosed invention is to provide a sampling device incorporated with a mechanism to facilitate transfer of the collected specimen to a preservative solution with minimal exposure to external contact therefore greatly reduces the likelihood of cross-contamination. Preferably, the disclosed invention uses a "pull and push" mechanism to unlock and transfer the cell collecting construct to the preservative solution.

Further object of the disclosed invention is to provide a relatively safer approach to deploy the cell collecting construct in the cervix for sampling. Preferably, the cell collecting construct is not collapsible within the protective sleeve along with retraction of the construct into the sleeve. No additional friction is generated during retraction of the construct to avoid accidental dislodge of the construct in the cervix.

At least one of the preceding objects is met, in whole or in part, by the present invention, in which one of the embodiments of the present invention involves a cervical cells sampling kitdevice comprising a tubular sleeve with a first opening and an opposing second opening; an elongate rod having a retractable part with a mounting tip enclosed within the sleeve and a handle section extending out from the sleeve through the second opening; a cell collecting construct with a resilient sheath being stretched to cap onto the mounting tip of the rod and the stretched resilient sheath is in a constant contracting state that the cell collecting construct and portion of the retractable part are allowed to project out or retract into sleeve through the first opening by moving the handle section; and a stripping member fabricated within the sleeve being fashioned to detach the resilient sheath from the mounting tip upon retracting the retractable part into the sleeve up to a predetermined level, wherein the resilient sheath of the construct resumes original form once detached from the mounting tip and prodding the rod back into the sleeve pushes the construct out of the sleeve.

In another preferred embodiment, the disclosed invention includes as well a cell preservative solution for soaking and preserving cell collected on the construct. Particularly, the cell collecting construct with the extracted cell specimen are stored within the solution until being processed further.

To optimize yield of the acquired cells, the construct preferably has a protruding body extended from the opposing end of the sheath and a plurality of appendages raised from the side of the protruding body to substantially surround the tip of the protruding body.

In one embodiment, a handling knob is attached on the handle section to render the user with better gripping onto the handle section while operating the disclosed invention. Likewise, the sleeve is fabricated with projection circumferentially extending out from outer rim of the sleeve. The circumferential projection serves as platform to allow the user hold better onto the sleeve during sampling.

In another embodiment, the disclosed invention has a retaining mechanism to prevent the rod being dissociated from the sleeve through the second opening.

Still another embodiment, the cell collecting construct is not collapsible upon withdrawal into the sleeve to avoid accidental dislodge of the construct in the vagina.

DETAILED DESCRIPTION OF THE INVENTION

Figure 1:
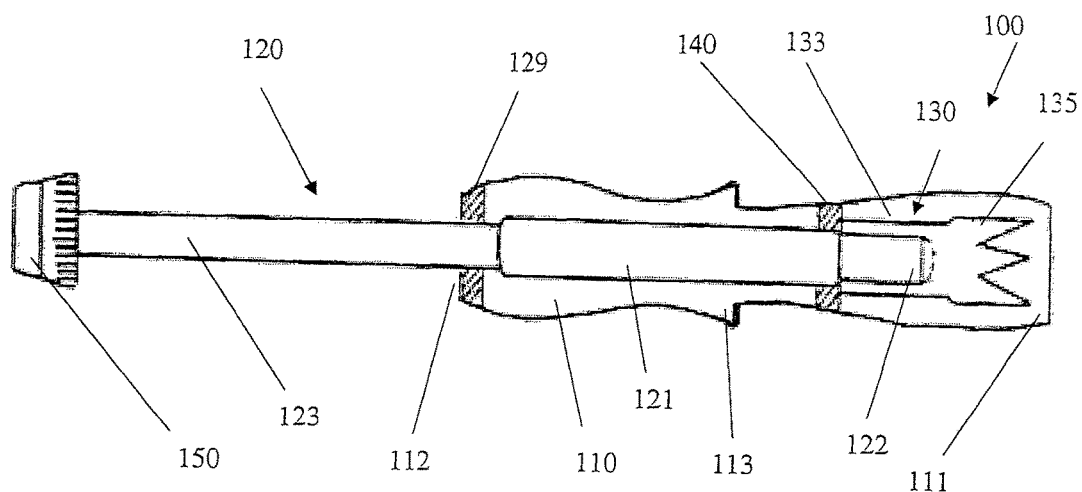
FIG. 1 is a cross-sectional view of one embodiment of the disclosed invention.

The most preferred embodiment of the invention is now described with reference to the figures, where like reference numbers indicate identical or functionally similar elements. While specific configurations and arrangements are discussed, it should be understood that this is done for illustrative purposes only. A person skilled in the art will recognize that the other configurations and arrangements can be used without departing from the scope of the invention.

One embodiment of the present invention is a cervical cells sampling device (100) comprising a tubular sleeve (110) with a first opening (111) and an opposing second opening (112); an elongate rod (120) having a retractable part (121) with a mounting tip (122) enclosed within the sleeve (110) and a handle section (123) extending out from the sleeve (110) through the second opening (112); a cell collecting construct (130) with a resilient sheath (133) being stretched to cap onto the mounting tip (122) of the rod (120) and the stretched resilient sheath (133) is in a constant contracting state that the cell collecting construct (130) and portion of the retractable part are allowed to project out or retract into sleeve (110) through the first opening (111) by moving the handle section (123); and a stripping member (140) fabricated within the sleeve (110) being fashioned to detach the resilient sheath (133) from the mounting tip (122) upon retracting the retractable part into the sleeve (110) up to a predetermined level, wherein the resilient sheath (133) of the construct (130) resumes original form once detached from the mounting tip (122) and prodding the rod (120) back into the sleeve (110) pushes the construct (130) out of the sleeve (110). Preferably, the cervical sampling device (100) may be in whole or by part fabricated from silicon material especially the part of the device (100) in which potentially in contact with cervix.

According to the preferred embodiment, the elongate rod (120) is made of material which is flex and resilient in nature to permit necessary bending to conform contour of the vaginal wall when the disclosed invention is inserted to the vagina. Nevertheless, the rod (120) may be produced from rigid or semi-rigid material in other embodiments as long the sleeve (110) provides sufficient space within for the retractable part going upward until the cervix to acquire the needed specimen. As in setting forth mentioned, the elongate rod (120) generally has one portion, the retractable part, enclosed within the sleeve (110) that the retractable part is the rod (120) portion to be inserted into the vagina under the shield of the sleeve (110). The retractable part ends into the mounting tip (122) serves as a point for the attachment of the cell collecting construct (130) through the sheath (133). Preferably, the diameter of the mounting tip (122) is slightly larger than the sheath (133) in order to have the sheath (133) stretched to cap onto the tip (122). The attachment of the cell collecting construct (130) on the mounting tip (122) can be improved by creating additional friction in between the contact of the sheath (133) and the tip (122). For example, the surface of the mounting tip (122) may be made abrasive or bearing slight lateral protrusion to impart greater friction. From the retractable part, the rod (120) extends out of the sleeve (110) to form the handle section (123) which is the spot for user to grip on and control the position of the attached cell collecting construct (130) in relative to the sleeve (110). It is important to be noted herein that there clear definition in terms of borders for the retractable part and the handle section (123) especially at the portion of the rod (120) around the second opening (112). Particularly, portion of the retractable part can be drawn out of the sleeve (110) upon pulling the handle section (123) to dislodge the cell collecting construct (130). Likewise, sampling within the user needs portion of the handle section (123) to be slid into the sleeve (110). Further, the rod (120) may bear a mark which only reveal to the user upon pulling the rod (120) to a level about to detach the cell collecting construct (130). The mark serves as an indicator to prompt the user the relative length of the retractable part within the sleeve (110) and further pulling may lead to detachment of the cell collecting construct (130).

Figure 2:
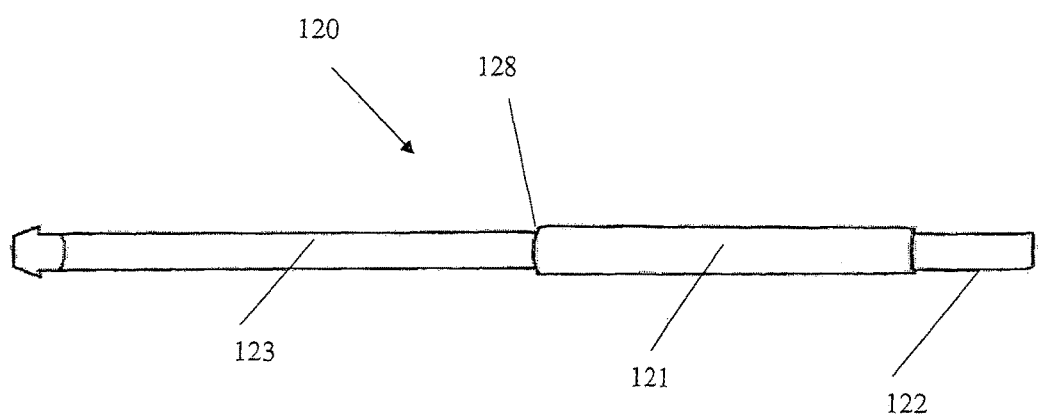
FIG. 2 shows the rod used in the embodiment of FIG. 1.

In another embodiment, the disclosed device (100) further comprises a handling knob (150) attached on the handle section (123). The handling knob (150) allows the user to have better grip onto the handle section (123). Shown in FIG. 2, in one embodiment, the handling knob (150) is a substantially round flat piece defining a threaded tunnel around its center while corresponding threaded track is found on the tip (122) of the handle section (123). The handling knob (150) can secure onto the handle section (123) through mating to the threaded track on the tip (122). Apart from that, fastening mechanism may not be required. Instead, the handling knob (150) may be manufactured together with the rod (120) as a single piece in other embodiment.

Figure 3:
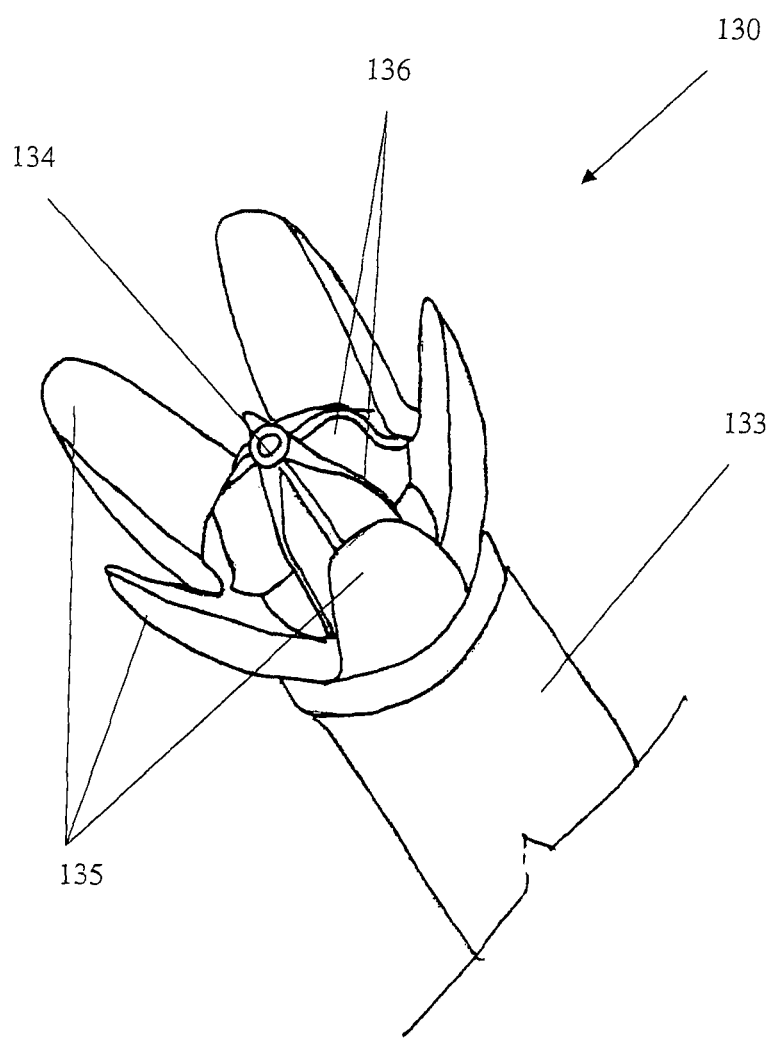
FIG. 3 shows one embodiment of the cell collecting construct.

Shown in FIG. 3, the sleeve (110) of the present invention is a tubular structure defining a hollow passageway accessible through two different openings, namely the first (111) and the second openings (112). These opening are located at both opposing ends of the sleeve (110). While the sleeve (110) being inserted into vagina of a user for sampling cervical cells, the hollow passageway allows the cell collecting construct (130) to be retracted into the passageway once the sample task completed thus protecting the collected specimen from being contaminated by withdrawal. The retracted rod (120) together with the sleeve (110) are drawn out of the user body once the sampling is done. Preferably, the sleeve (110) is made of semi-rigid material that it can bend slightly to conform the shape of the vaginal wall therefore inflicting less comfort feeling to the user. The end of the sleeve (110) carrying with the first opening (111) is the end to be inserted into the vagina for sampling. Together with the enclosed rod (120), the sleeve (110) moves upward until reaching the cervix followed by the cell collecting construct (130) being extended out of the sleeve (110) to contact and acquire cell sample from the cervix. One embodiment of the disclosed device (100) has the sleeve (110) slightly tapered towards the first opening (111) to ease the penetration of the sleeve (110) into the vagina. More preferably, the edge of the first opening (111) avoids substantial sharp edge to lessen the discomfort.

In one preferred embodiment, the first opening (111) is relatively larger than the second opening (112) in order to fully accommodate the cell collecting construct (130) without having the construct (130) collapse within the sleeve (110). The sleeve (110) may adapt a shape illustrated in FIG. 3 that its lower portion is relatively slim down in size compared to the upper portion. Considering that the attachment of the cell collecting construct (130) on the mounting tip (122) is solely based on contact friction in between the two objects, collapsing of the cell collecting construct (130) when retracting it back to a relatively smaller sleeve (110)

shall inflict inessential opposing force to rid the construct (130) off the mounting tip (122) and lead to potential detachment of the construct (130). Consequently, the cell collecting construct (130) of the disclosed device (100) is not collapsed upon withdrawal into the sleeve (110) in the most preferred embodiment.

Further, the external surface of the sleeve (110) carries a scale grading in one embodiment. The grading shows the user the total length of the sleeve (110) being penetrated through the vagina and the proper location to conduct the sampling via the cell collecting construct (130). Additionally, the sleeve (110) is fabricated with projection circumferentially extending out from outer rim of the sleeve (110) adjacent to the second opening (112). The user can grip on the circumferential projection using fingers to pull the sleeve (110) out of the vagina. Still, in another embodiment, the external surface of the sleeve may be fabricated with abrupt circumferential enlargement (113) around the middle section to serve as an indicator to remind the user not to push the sleeve into the vagina beyond the indicator as further proceeding into the vagina thereon may lead to great discomfort.

Internally, the sleeve (110) carries the stripping member (140) inside the through passageway to remove the sheath (133). It is important to be noted herein that the stripping member (140) can take many forms or shapes to attain the similar purpose. Particularly, the stripping member (140) is a structure which generates an external force to pull the cell collecting construct (130) away from the mounting tip (122) in line with pulling the rod (120) out of the sleeve (110) from the second opening (112). Since the sheath (133) is capped onto the mounting tip (122), the area of the mounting tip (122) covered with the sheath (133) is relatively thicker than the rest of the rod (120) starting from the rim or edge of the sheath (133). Thus, the disclosed device (100) fashions the stripping member (140) to define a small aperture merely approximates to the diameter of the rod (120), or at least approximates to the diameter to mounting tip (122) that thickness more than the aperture defined is prohibited to pass through. For example, the stripping member (140) can be a single layer perpendicularly converging towards the center of the passageway defining an aperture sized to barely pass the rod (120) and/or the mounting tip (122) but not the mounting tip (122) capped with the sheath (133). Upon the edge of the sheath (133) abutting onto the layer of the stripping member (140), further pulling force at the handle section (123) compels the sheath (133) sliding off the mounting piece as long the pulling force is greater than the friction in between the mounting tip (122) and the sheath (133). With sufficient pulling force, the cell collecting construct (130) is detached from the mounting tip (122) and retained within the sleeve (110). In other embodiment, the stripping member (140) can be simply a pair of opposing protrusion perpendicularly deriving from the inner wall of the sleeve (110) roughly define a gap to merely pass the mounting tip (122) and/or the rod (120). Similarly, the protrusion removes the stretched sheath (133) thereof when the rod (120) is pulled to pass through the gap. Once it is detached from the mounting tip (122), the sheath (133) contracts and resumes its original size. The mounting tip (122) fails to fit into the sheath (133) again unless an external force laterally stretches the sheath (133). Thus prodding the rod (120) back into the sleeve (110) pushes the cell collecting construct (130) out of the sleeve (110) rather than attaching the sheath (133) onto the mounting tip (122) again. Further, misalignment of the sheath (133) from the defined gap or aperture further reduces the likelihood of the re-attachment. With the way the cell collecting, construct (130) being fixed to the mounting tip (122), the disclosed device (100) minimizes the acquired cell sample from exposing to unnecessary contact in between the sampling and transfer of the cell specimen.

Moreover, the disclosed invention is preferably incorporated with a retaining mechanism to prevent the rod (120) being dissociated from the sleeve (110) through the second opening (112). To realize the retaining mechanism, the retractable part is fabricated with projecting rib (128) flanking at the side surface of the rod (120). The projecting rib (128) is positioned at a level lower than the stripping member (140) in the operative mode of the disclosed device (100) to avoid interfering with the mechanism to dislodge the cell collecting construct (130). Correspondingly, a secondary layer (129) perpendicularly stretching out from the inner surface of the sleeve (110) defining secondary aperture or gap to prohibit the projecting rib (128) to slide through but not the rest of the rod (120). The projecting rib (128) and the secondary layer (129) collectively form the retaining mechanism to stop the rod (120) from being dissociated from the sleeve (110). The projecting rib (128) is only able to reach the secondary layer (129) after detachment of the cell collective construct (130). Besides serving as a barrier, both the stripping member (140) and the secondary layer (129) align the sliding movement of the rod (120) in the sleeve (110).

Illustrated in FIG. 3 is one embodiment of the cell collecting construct (130) used in the disclosed device (100) to acquire both exocervical and endocervical cells. Preferably, the construct (130) has a protruding body (134) extended from the opposing end of the sheath (133) and a plurality of appendages (135) raised from the side of the protruding body (134) to substantially surround the tip (122) of the protruding body (134). As in the foregoing, the cell collecting construct (130) is produced from resilient material especially permitting the appendages (135) to be bent and later resuming its original form in the sampling operation. More preferably, the appendages (135) substantially shield the protruding body (134) upon collapsing the appendages (135) towards the central axis of the construct (130) when the cell collecting construct (130) is withdrawn into the tubular sleeve (110). It is important to be noted that the protruding body (134) of the construct (130) aims to acquire endocervical cells while the appendages (135) targets for the exocervical cell. In one embodiment, the protruding body (134.) is a plurality of upstanding fins (136) equally spaced apart at an angle in the horizontal planar that each fin has one side edge joined together substantially at the central axis of the construct (130) as shown in FIG. 3. The fins (136) stretch out horizontally from the conjoined edges located at the central axis of the cell collecting construct (130). The tip of the protruding body (134) can be inserted into the endocervical cavity to collect ectocervical cell. Particularly, the elongate rod (120) is slightly turned to rotate and scrap some of the ectocervical cells onto the fin surface once the protruding body (134) reaches into the endocervical cavity. Meanwhile, the inner surfaces of the appendages (135) shall press against the external os to retrieve the exocervical cells. One of the preferred embodiment has the appendage tapered towards its end from the base joined to the protruding body (134) and the end of the appendages (135) are slightly tiled outward to facilitate cell collection within its inner surface. Having the specimen sampled within the inner surface of the appendages (135) avoids specimen loss when the cell collecting construct (130) is retracted back into the sleeve (110). As mentioned above, the sheath (133) extends underneath the protruding body (134) defining a recess within to be stretched to accommodate the mounting tip (122).

According to another preferred embodiment, the sampling device (100) further includes a cell preservative solution for soaking the construct (130) being pushed out of the sleeve (110). The preservative solution containing isotonic and preservative solution.

One skilled in the art will readily appreciate that the present invention is well'adapted to carry out the objects and obtain the ends and advantages mentioned, as well as those inherent therein. The embodiments describes above are not intended as limitations on the scope of the invention.

The invention claimed is:

1. A cervical cells sampling device, comprising:
   a tubular sleeve with a first opening at a first end of said tubular sleeve and a second opening at a second end of said tubular sleeve;
   an elongate rod having a retractable part with a mounting tip enclosed within said tubular sleeve and a handle section extending out from said tubular sleeve through the second opening, so that a portion of said retractable part is able to project out of, or be retracted into, said tubular sleeve through the first opening of said tubular sleeve by moving said handle section;
   a cell collecting construct with a resilient sheath that is stretchable and stretched to cap onto said mounting tip of said elongate rod and said resilient sheath, as stretched and remains stretched, so that said cell collecting construct and a portion of the retractable part are allowed to project out or retract into said tubular sleeve through the first opening by moving said handle section; and,
   a stripping member within said tubular sleeve for detaching said resilient sheath from said mounting tip upon retracting said retractable part into said tubular sleeve to a predetermined position, wherein said resilient sheath of said cell collecting construct resumes an unstretched form once detached from said mounting tip and placing said elongate rod back into said tubular sleeve pushes said cell collecting construct out of said tubular sleeve, wherein said elongate rod pushes out said resilient sheath from said tubular sleeve through the first opening after said resilient sheath is dismounted from said mounting tip,
   wherein, said cell collecting construct has a protruding body extending from an end of said cell collecting construct that is opposite, or opposed to, said resilient sheath and a plurality of appendages extend from a side of said protruding body for substantially surrounding said protruding body.

2. The cervical cells sampling device according to claim 1, wherein said protruding body is a plurality of upstanding fins equally spaced apart and disposed at an angle in a horizontal plane relative to a surface perpendicular to a central axis of said cell collecting construct, wherein each fin of said plurality of upstanding fins has one side edge joined together substantially at the central axis of said cell collecting construct.

3. The cervical cells sampling device according to claim 1, wherein said plurality of appendages substantially shield said protruding body upon collapsing said plurality of appendages toward a central axis of said cell collecting construct.

4. The cervical cells sampling device according to claim 1, wherein said plurality of appendages is tapered.

* * * * *